United States Patent [19]
de Castro et al.

[11] Patent Number: 5,104,619
[45] Date of Patent: Apr. 14, 1992

[54] DISPOSABLE DIAGNOSTIC SYSTEM

[75] Inventors: Aurora F. de Castro, Union, Mich.; Surendra K. Gupta, Elkhart, Ind.; William J. McLaughlin, Indianapolis, Ind.; David E. Storvick, Greenwood, Ind.

[73] Assignee: GDS Technology, Inc., Elkhart, Ind.

[21] Appl. No.: 628,348

[22] Filed: Dec. 17, 1990

Related U.S. Application Data

[63] Continuation-in-part of Ser. No. 469,920, Jan. 24, 1990.

[51] Int. Cl.⁵ .............................................. G01N 31/22
[52] U.S. Cl. ...................................... 422/56; 422/57; 422/58; 422/101; 422/102; 436/169
[58] Field of Search ................................. 422/56–58, 422/101, 102; 435/805; 436/169

[56] References Cited

U.S. PATENT DOCUMENTS

| | | | |
|---|---|---|---|
| 4,365,970 | 12/1982 | Lawrence et al. | 422/58 X |
| 4,592,893 | 6/1986 | Poppe et al. | 422/56 |
| 4,738,823 | 4/1988 | Engelmann | 422/56 |
| 4,797,260 | 1/1989 | Parker | 422/101 |

Primary Examiner—Jill Johnston
Attorney, Agent, or Firm—Browdy and Neimark

[57] ABSTRACT

A disposable diagnostic assembly or device for performing diagnostic tests which include test card and strip structures having a generally flat area, containing a well with an interior wall defining a reagent pad pocket to receive a specifically designed chemical reagent pad and which is secured in place by an annular snap-on cover. Additionally, the test card or strip may have a raised rib to contain spilled sample fluid. The diagnostic assembly is used to measure the concentration of an analyte via visualization or in combination with a meter.

35 Claims, 6 Drawing Sheets

DISPOSABLE DIAGNOSTIC SYSTEM

BACKGROUND OF THE INVENTION

This is a continuation-In-Part of application Ser. No. 07/469,920, filed Jan. 24, 1990.

The present invention provides a disposable diagnostic system designed to receive reagent chemistry to measure the concentration of analytes. The system includes a card device or assembly which can be conveniently measured visually or by a meter. This measurement, either by the visual comparison of color or in combination with a meter utilizing a software algorithm to measure a signal, such as color, provides a user-meaningful analyte concentration reading. The disposable diagnostic assembly comprises a rigid or semi-rigid card or strip structure of a predetermined configuration and size. The card or strip structure comprises a snap-closed well or pocket wherein a reagent chemistry pad is arranged and which provides for the freedom to change the pad chemistry. The diagnostic system of this invention provides a user with means of producing an economical, safe and simple test that can be conducted by a wide range of personnel and under a wide range of conditions.

In the past, diagnostic tests have been performed in a variety of ways and employing a variety of devices and related equipment. For example, disposable diagnostic products are used by diabetics who need to monitor blood glucose levels. These types of blood glucose strips typically comprise disposable, long, narrow plastic strips having chemical reagent pads adhesively secured to one end. The addition of a dose of blood onto the reagent pad of the glucose strip produces a color change which is measured by eye or by a meter to indicate the concentration of glucose in the blood.

The prior art disposable strip devices, however, have many limitations. For example, (a) body fluid may contaminate the area where testing is performed, the meter utilized and, thus, the hands of the operator; (b) it is difficult to provide incompatible reagent ingredients or chemistry involving different pHs in such formats containing only one layer; (c) certain adhesives used in prior art devices to hold layer(s) together, for example, may interfere with the reagent chemistry; and (d) the configuration of some prior art systems are prone to improper positioning in a meter which can result in erroneous test results. The present invention provides a system that overcomes these prior art problems and limitations and provides an easy to use diagnostic device or assembly of significant benefit.

Various diagnostic and immunoassay devices and methods are known in the art, such as those disclosed in U.S. Pat. No. 3,635,679 (Bloch et al.), U.S. Pat. No. 3,876,378 (Montagnon), U.S. Pat. No. 4,059,405 (Sodickson), U.S. Pat. No. 4,366,241 (Tow et al.), U.S. Pat. No. 4,444,193 (Fogt et al.), U.S. Pat. No. 4,522,923 (Deutsch et al.), U.S. Pat. No. 4,632,901 (Valkirs et al.), U.S. Pat. No. 4,717,656 (Swanljung), U.S. Pat. No. 4,727,019 (Valkirs et al.), U.S. Pat. No. 4,769,333 (Dale et al.), U.S. Pat. No. 4,797,260 (Parker), U.S. Pat. No. 4,818,677 (Hay-Kaufman et al.), and U.S. Pat. No. 4,857,453 (Ullman et al.). The devices disclosed in these patents are typically cumbersome to use, not disposable, and are structurally different from that of the present invention.

Further, U.S. Pat. No. 4,790,979 (Terminello et al.) describes a test strip involving a wicking element for reception of a whole blood sample, a barrier layer, and a porous membrane impregnated with dry chemistry reagents. U.S. Pat. No. 3,791,933 (Moyer et al.) discloses a test system consisting of several complex elements for determining an enzyme substrate and metabolites. U.S. Pat. Nos. 3,990,850 and 4,055,394 (Friedman et al.) disclose diagnostic test cards which involve folding an end flap to observe test results. U.S. Pat. No. 4,587,102 (Nagatomo et al.) describes a multilayer analysis element utilizing specific binding reactions. U.S. Pat. No. 3,809,617 (Schmitt) describes a device for detecting anticholinesterase. U.S. Pat. No. 4,477,575 (Vogel et al.) describes a process for separating plasma or serum from whole blood. U.S. Pat. No. 4,256,693 (Kondo et al.) provides a multilayered integral chemical analysis element for blood. U.S. Pat. No. 4,738,823 (Engelmann) describes a test strip device with adjustable sample absorption capacity for the purpose of quantitating the sample volume.

Although a variety of devices and methods are disclosed in the foregoing prior art patent references, none show or suggest a disposable diagnostic test system to incorporate reagent chemistry according to the teachings of the present invention.

SUMMARY OF THE INVENTION

The disposable diagnostic assembly according to the present invention comprises a test card or strip including a substantially flat body, a generally cylindrical reagent pad pocket formed in the central area, a reagent chemistry pad(s) disposed in the pocket and a snap-fit cover received in the pocket and arranged over the pad to retain the pad in position. Additionally, the test card or strip may contain a raised rib which serves to contain any spilled fluid, such as blood, to eliminate possible contamination.

The device structure of this invention further has a configuration so that it can be placed in a meter having an indented surface to receive the device well so as to provide an exact placement of the device structure in the optical path to, thereby, prevent reading errors. Additionally, the device structure does not require the use of adhesives to maintain the chemistry pads in position.

The object of the present invention is to provide an improved disposable diagnostic assembly which can be conveniently used to measure various analytes in the body, quantitatively or qualitatively, and visually or instrumentally.

Related objects and advantages of the present invention will be apparent from the following description.

DESCRIPTION OF THE PREFERRED EMBODIMENTS

This invention relates to a disposable diagnostic test system comprising a device or assembly consisting of a generally flat body surface, which can be rigid or semi-rigid, can be made of plastic, such as polystyrene, polypropylene, or the like, and which can be easily formed, such as by injection molding or thermoforming processes. The test card has a well or pocket with an interior wall defining a reagent pad pocket to contain at least one specifically designed reagent pad or matrix, and a retaining structure, such as a cap, cover or lid to secure the pad in place. The purpose of the integral retaining structure or lid is to fix the pad(s) in the well or pocket and is to provide desired positive pressure so that the reagent pad(s) are in intimate contact with each other without the need of any adhesives or any other means. The well may be cylindrical or rectangular in configuration and is constructed and arranged to fit into an appropriate female recess or fitting on a meter reading surface. The cap has an aperture to receive a sample. The well has a bottom aperture to visually or instrumentally observe the reaction that has occurred in the reagent pad when the sample has been applied. If the test device material is transparent such well bottom aperture may not be required.

The method employed by the device consists of applying the sample to the cover aperture and allowing the sample to react with the reagent pad or laminated pads within the reagent pad pocket, and then observing the reaction signal, such as color, through the bottom surface or aperture of the pocket or well. The reaction signal can be measured visually providing semi-quantitative results or instrumentally providing quantitative results.

This device and method can be used employing chemical, enzymatic or immunochemical reactions for the measurement of substances, such as analytes in fluids, including body fluids. For example, the device can be used to measure blood metabolites, such as glucose, cholesterol, uric acid, triglycerides; enzymes, such as, lactase dehydrogenase, creatine kinase; hormones, such as, thyroxine, progesterone; and drugs, such as theophylline, acetaminophen, cocaine, or the like. In addition, other fluid samples containing chemicals, such as toxic phenolic compounds, or heavy metals, for example, can also be measured.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates. For example, the diagnostic system may be utilized for medical as well as non-medical purposes.

Figure 20:
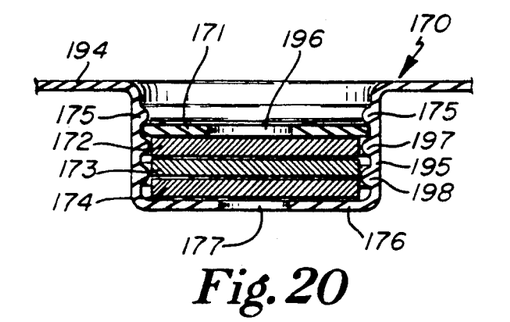
FIG. 20 is a cross-sectional view of a well showing another embodiment of the diagnostic testing system of this invention.
Figure 21:
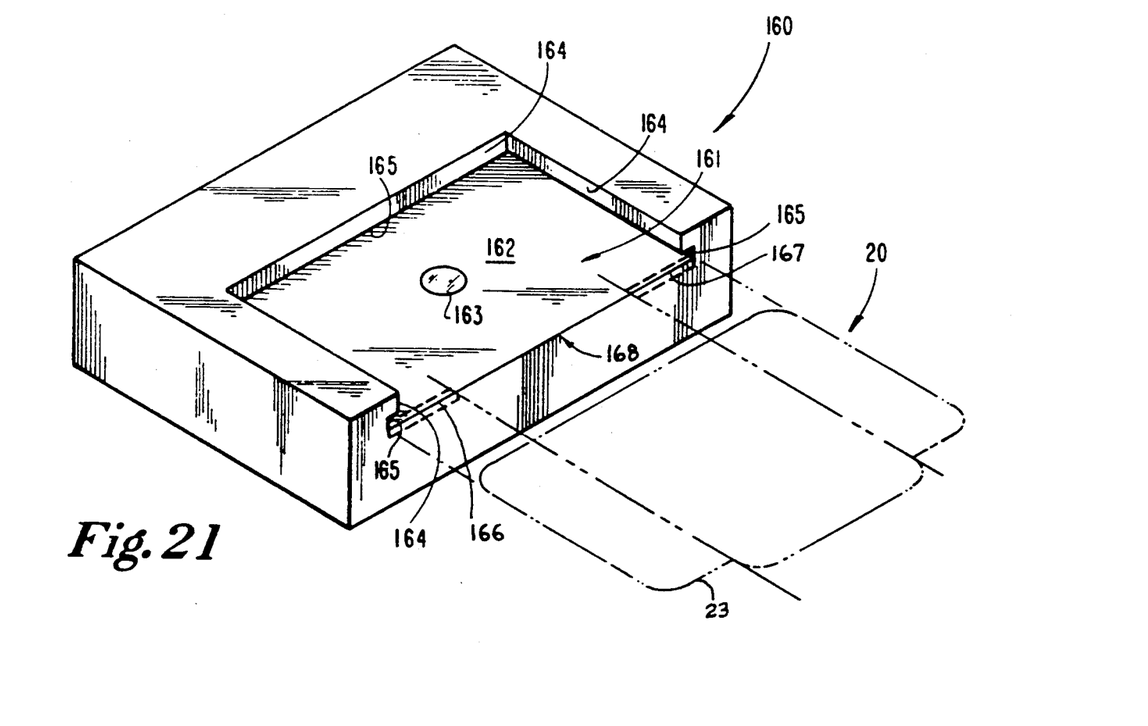
FIG. 21 is a perspective view of a reflectance-type meter suitable for use with a test card of the present invention incorporating a software algorithm and providing user-meaningful concentration data.
Figure 22:
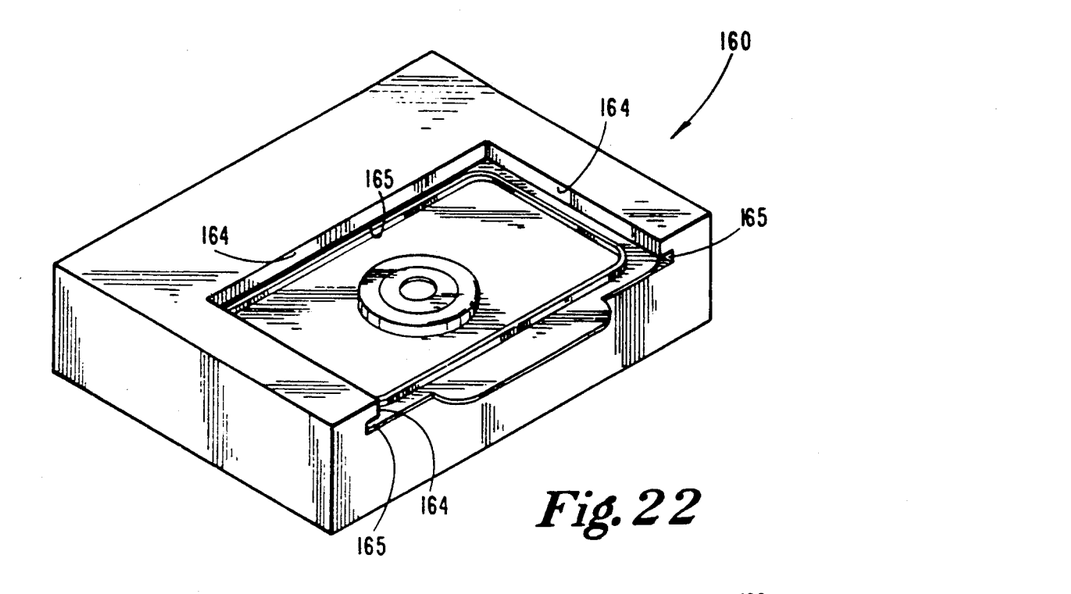
FIG. 22 is a perspective view of the FIG. 21 meter with a test card (FIG. 1 or FIG. 8) inserted in a card-reading orientation.

Referring to FIGS. 1-5, there is illustrated a disposable diagnostic test card 20 which is designed to receive a customer's specific reagent chemistry (see FIGS. 15 and 20 for examples of typical reagent pads) and used with a reflectance-type laboratory meter (see FIGS. 21 and 22). As will be explained further, the color change of the reagent chemistry pad when reacted with whole blood or other liquid is measured by the meter or alternatively by direct visualization by a technician. A software algorithm within the meter electronics converts the remission reading to a user-meaningful concentration reading such as milligrams per deciliter (mg/dL).

Test card 20 (FIG. 1) is preferably a single piece, injection molded or thermoformed plastic member which is generally rectangular and specifically contoured in order to provide various features. The nominal material starting thickness throughout the test card is approximately 0.02 inches (0.51 mm) and an exemplary material is polystryrene. Test card 20 (FIG. 1) includes an outer perimeter lip 21 which blends into integral tab 22 which is centered on the front edge 23 of the card. The test card 20 is shown to have a raised rib 24, uniformly inset from the outer perimeter edge, which extends approximately to 0.06 inches (1.52 mm) above top surface 25. The raised rib is uniformly inset such that the width of the perimeter lip is substantially the same throughout the perimeter of the test card with the noted exception of the front tab 22. The overall length of the test card is approximately 2.6-3.50 inches (66.0-88.9 mm) and the body width is approximately 1.5-2.0 inches (38.1-50.8 mm). These card dimensions are exemplary and other card sizes depending upon desired use can also be utilized within the purview of this invention. The test card 20 is also shown to have a tab 22 which provides an easy to use handle for convenience as well as to provide further safety to the operator as it keeps the fingers away from the possible contaminated surface within the rib area. In addition, this area can be used as a patient identification feature providing a place to write the patient's name.

The center area of test card 20 (FIG. 1) includes a raised cylindrical portion 29 whose interior annular wall is uniquely shaped and contoured for this particular application. Portion 29 can be thought of as both a raised and recessed annular member which is hollow having opening 30 extending therethrough. With this description it is to be understood that opening 30 which is intended to denote the entire open area in the center of portion 29 has a varying diameter size as it extends from the larger top opening area to the smaller opening in the bottom surface.

Figure 1:
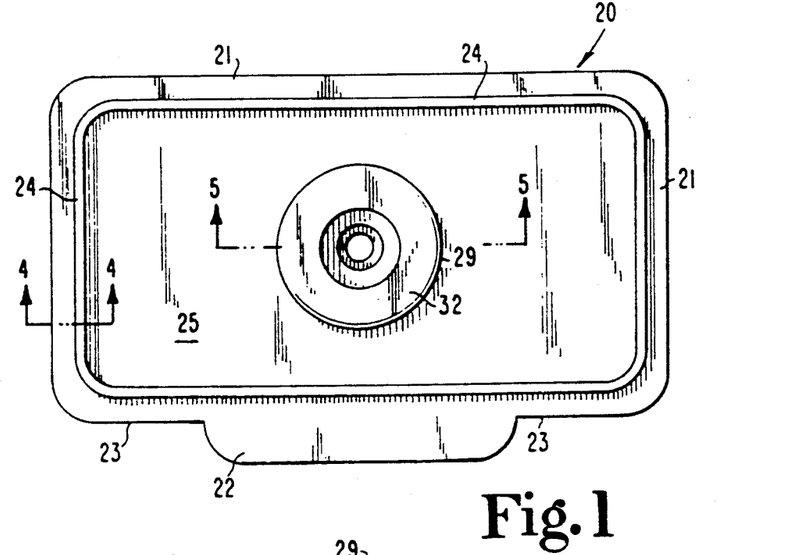
FIG. 1 is a top plan view of a disposable diagnostic test card according to a typical embodiment of the present invention.
Figure 2:
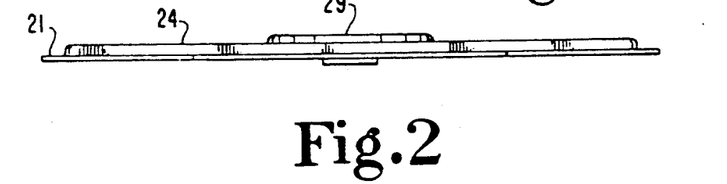
FIG. 2 is a front elevational view of the FIG. 1 test card.
Figure 3:
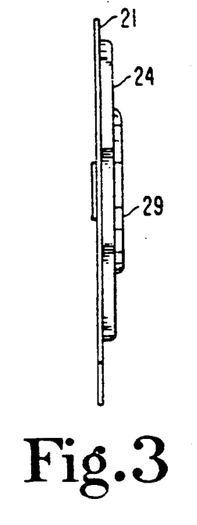
FIG. 3 is a side elevational view of the FIG. 1 test card.
Figure 4:
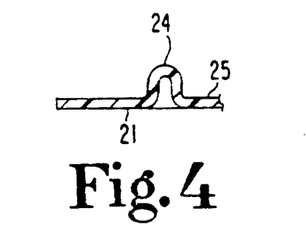
FIG. 4 is an enlarged section view as taken along line 4—4 in FIG. 1.
Figure 5:
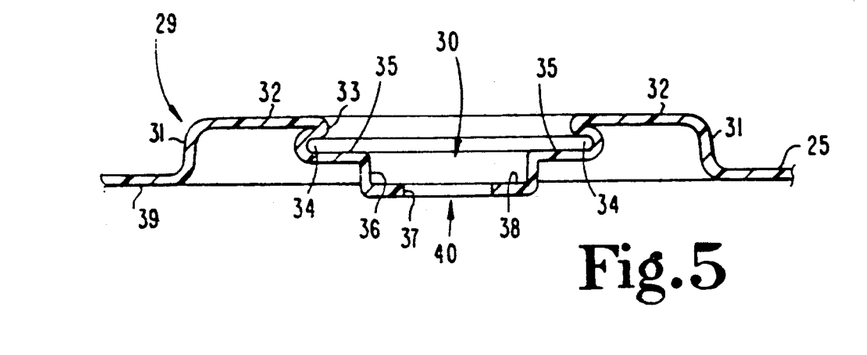
FIG. 5 is an enlarged section view as taken along line 5—5 in FIG. 1.
Figure 12:
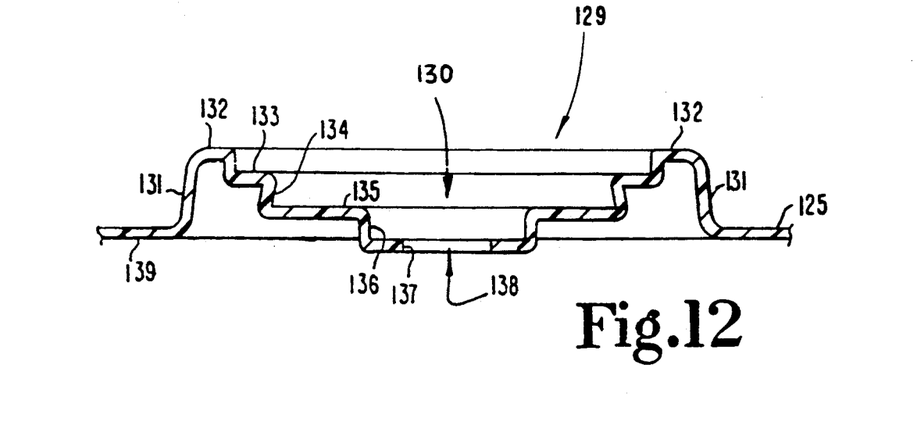
FIG. 12 is an enlarged section view as taken along line 12—12 in FIG. 8.

With specific reference to the enlarged cross-sectional detail of FIG. 5, cylindrical portion 29 includes an outer vertical wall 31, top surface 32, double thickness folded lip 33, undercut annular recess 34, upper horizontal shelf 35, inner vertical wall 36 and lower horizontal shelf 37. In view of the varying diameters constituting the wall portions which define opening 30, the opening changes in diameter size as it extends from the top surface 32 to shelf 37 which defines centrally therein lower aperture 40. The structures of FIGS. 5 and 12 are adapted to be fit or placed into a recessed area in the meter reading surface to receive the well portion and allowing for the tight optical alignment of the device which assists in increasing accuracy and precision of the results.

Another feature of portion 29 (FIG. 5) is that lower horizontal shelf 37 is disposed below top surface 25 of the main card. More specifically the upper surface 38 of shelf 37 is coincident with the underside 39 of top surface 25. Thus with a nominal material thickness of 0.02 inches (5.1 mm) for shelf 37, the lower surface of shelf 37 is approximately 0.02 inches (5.1 mm) below underside 39. This arrangement assures that the reagent area will be exposed to the measuring light beam when the device is placed in a meter. Although this nominal thickness has been found useful to form test cards, other thicknesses depending upon material composition can also be utilized. However, if the material is significantly thicker, an inwardly beveled surface as viewed from the bottom may be formed at the peripheral edge of 37 to allow more light to be reflected from the reagent area. As will be further described, the shelf member 37 may also be spatially positioned differently with respect to the top surface 25.

The outside diameter of portion 29 (FIG. 5) is approximately 0.94 inches (23.85 mm) and its height above underside 39 is approximately 0.12 inches (3.05 mm). The inside diameter of lip 33 is approximately 0.44 inches (11.18 mm) and the diameter of recess 34 is approximately 0.52 inches (13.21 mm). The result of these dimensions creates an overhang width for lip 33 of approximately 0.04 inches (1.02 mm). These latter dimensions are also exemplary and can be varied depending upon material composition and test card use.

Figure 6A:
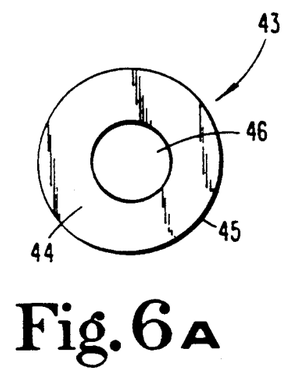
FIG. 6A is a top plan view of a test card cover comprising a portion of the present invention and suitable for use in combination with the FIG. 1 test card.
Figure 6B:
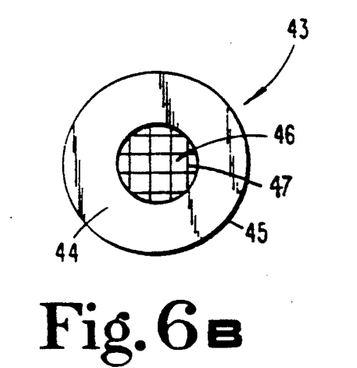
FIG. 6B is a top plan view of another embodiment of a test card cover for use in this invention.
Figure 7:
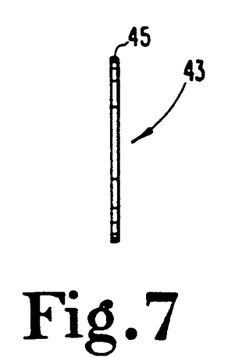
FIG. 7 is a side elevational view of the covers of FIGS. 6A and 6B.
Figure 8:
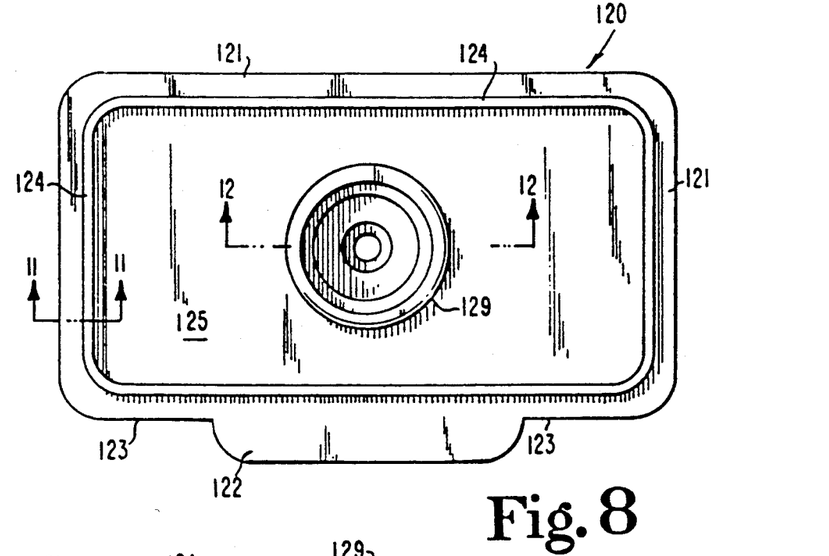
FIG. 8 is a top plan view of a disposable diagnostic test card according to a typical embodiment of the present invention.
Figure 9:
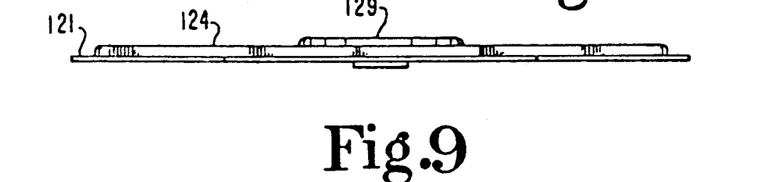
FIG. 9 is a front elevational view of the FIG. 8 test card.
Figure 10:
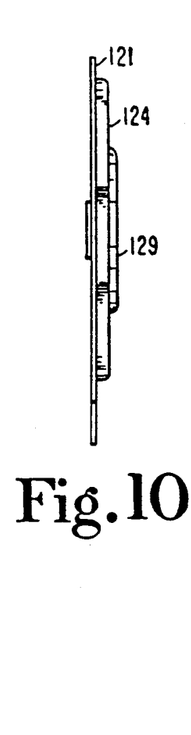
FIG. 10 is a side elevational view of the FIG. 8 test card.
Figure 11:
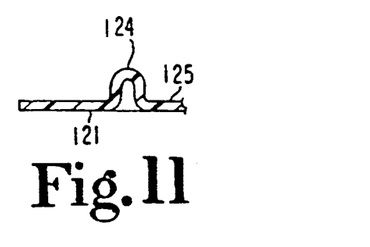
FIG. 11 is an enlarged section view as taken along line 11—11 in FIG. 8.
Figure 15:
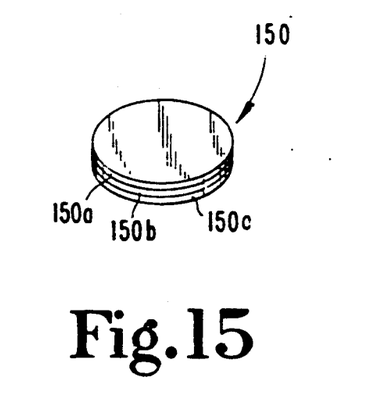
FIG. 15 is an enlarged perspective view of a chemistry reagent pad including a plurality of laminations.

Referring also to FIG. 15, test card 20 (FIG. 1) is used as a receptacle or holder for a reagent chemistry pad which fits within opening 30 (FIG. 5). More specifically, the pad which is cylindrical so as to match the shape of the receiving pocket of portion 29 (FIG. 5) typically includes a plurality of laminations, in the illustrated embodiment there are three, and this reagent chemistry pad rests on surface 38 of shelf 37 and is flush with to slightly recessed below shelf 35. The reagent chemistry pad is captured by use of a snap-fit cover 43 as is illustrated in FIGS. 6A, 6B and 7. Cover 43 is an annular ring or disc of uniform thickness with a main body 44 defined by an outer edge 45 and inner circular opening 46. Opening 46 (FIGS. 6A and 6B) is shown to be coaxial with aperture 40 (FIG. 5). The opening 46 of cover 43 can also have a mesh or grid area 47, as illustrated in FIG. 6B. The mesh or grid area 47 may be formed integral with cover 43 or may be a separate structure subsequently fixed to cover 43. The grid area 47 is provided to impart a uniform retaining force to the reagent pad held in the opening or well 30.

In use, a pipette, for example, having a quantity of sample drops a quantity of sample into contact with the filter/matrix 171–174 (FIG. 20). After absorption of the fluid sample added, a reaction takes place and the bottom layer of the matrix changes its color to show the existence of a predetermined chemical component, which is viewable through the bottom aperture 177.

The color changes in the bottom layer of the filter/matrix 174 shows the qualitative existence of the specified chemical component in the sample. A quantitative measurement can then be effected by use of a color chart, as known in the art, having varying color bars or codes.

Referring again to FIGS. 1–7, the cover 43 is preferably constructed out of polystyrene and is sized and shaped to snap fit securely within undercut recess 34. The height or axial depth of recess 34 is approximately 0.025 inches (0.64 mm) and cover 43 is approximately 0.02 inches (0.51 mm) in thickness. Since the diameter of the recess is approximately 0.52 inches and the outer diameter of cover 43 is approximately 0.50 inches (12.7 mm), assembly without interference is, therefore, possible. As should be understood, as the size of the test card 20 is changed to accommodate different reagent chemistry pads and fit into different reflectance meters, the size of cover 43 must change accordingly to fit and snap into recess 34. Another option with regard to cover 43 in lieu of a snap-fit is to include a thin layer of adhesive on the underside as a means of attachment to the test card. The adhesive thickness is approximately 0.005 inches and a suitable material is a 3M ™ adhesive transfer tape 9469PC covered with a release liner on the exposed side.

Referring to FIGS. 8–12, there is illustrated a disposable diagnostic test card 120 which is designed to receive a customer's specific reagent chemistry (see FIGS. 15 and 20 for examples of typical reagent pads) and used with a reflectance-type meter (see FIGS. 21 and 22). As will be explained further, the color change of the reagent chemistry pad when reacted with whole blood or other liquid is measured by the meter. A software algorithm within the meter electronics converts the remission reading to a user-meaningful concentration reading such as milligrams per deciliter (mg/dL).

Test card 120 (FIG. 8) is preferably a single and unitary, injection molded or thermoformed plastic member, for example, which is generally rectangular and specifically contoured in order to provide various features. The nominal material starting thickness throughout the test card is approximately 0.02 inches (0.51 mm) and the preferred material is polystyrene, although, as will be later discussed, other materials may also be utilized. Test card 120 includes an outer perimeter lip 121 which blends into integral tab 122 which is centered on the front edge 123 of the card. Uniformly inset from the outer perimeter edge is a raised rib 124 which extends approximately to 0.06 inches (1.52 mm) above top surface 125. It is to be noted that with the exception of tab 122, the raised rib is uniformly inset such that the width of the perimeter lip is substantially the same throughout the perimeter of the test card with the noted exception of the front tab 122. The overall length of the test card is approximately 2.6–3.50 inches (66.0–88.9 mm) and the body width (without tab 122) is approximately 1.5–2.0 inches (38.1–50.8 mm). As discussed above, other card dimensions and sizes can also be utilized within the purview of this invention.

The center area of test card 120 (FIG. 8) includes a raised cylindrical portion 129 which has a contoured and uniquely shaped interior wall (annular) surrounding and defining center opening 130. As with test card 20, cylindrical portion 29 and opening 30, the annular wall of portion 129 has a number of surfaces, edges, bends and contours and is uniquely shaped to receive the chemistry reagent pad and an appropriate cover which is snapped over the cylindrical portion 129 in order to sandwich or retain the pad in position.

Figure 14:
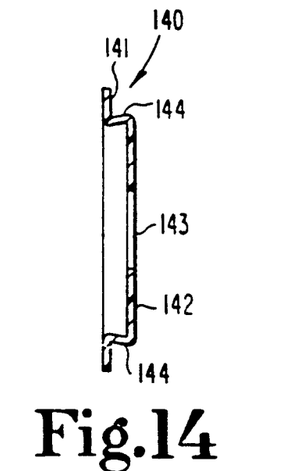
FIG. 14 is a full cross-sectional view of the FIG. 13 cover as taken along the line 14—14 in FIG. 13.

With specific reference to the enlarged cross-section detail of FIG. 12, portion 129 includes outer vertical wall 131, top surface 132, upper horizontal shelf 133, intermediate angled wall 134, intermediate horizontal 135, inner vertical wall 136 and lower horizontal shelf 137 which defines aperture 138. Similar to test card 20 the lower horizontal shelf 137 of test card 120 is disposed below top surface 125 such that the top surface of shelf 137 is coincident or flush with the underside 139 of top surface 125. Wall 134 is angled or tapered outwardly from top to bottom at a 10 degree slant so as to be compatible with tapered side wall 144 of cover 140 (FIG. 14).

Figure 13:
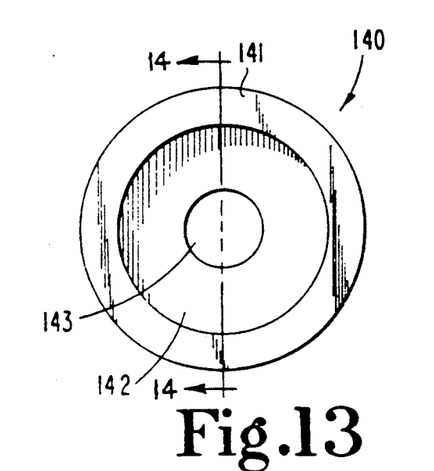
FIG. 13 is a top plan view of a test card cover according to the present invention and suitable for use with the FIG. 8 test card.

Due to the different configuration of opening 130 in test card 120 (FIGS. 8–12) as compared to opening 30 in test card 20 (FIGS. 1–5), a slightly different cover 140 (see FIGS. 13 and 14) is used with card 120. Cover 140 which has a cylindrical shape includes an outer circular lip 141 and a raised cylindrical center portion 142 with a defined opening 143 therein. Portion 142 has a slightly (10 degrees) tapered side wall 144 which snaps into the area of portion 129 defined by wall 134 and shelf 135. The reagent chemistry pad (FIGS. 15 or 20) fits in the area defined by wall 136 and shelf 137. The diameter and thickness of lip 141 is such that it fits snugly onto outer shelf 133 and intermediate shelf 135 and as assembled, the top surface of lip 141 is substantially flush with top surface 132. Opening 143 is coaxial with aperture 138.

Figure 16:
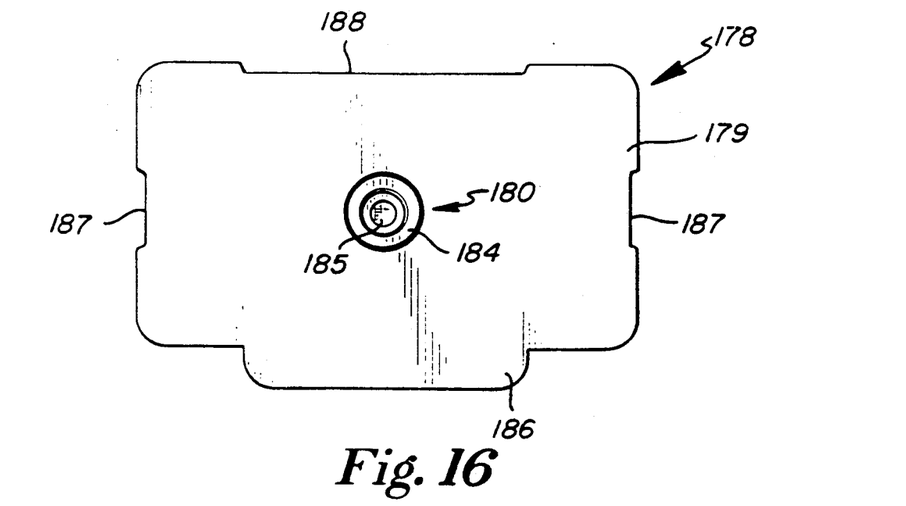
FIG. 16 is a top view of another embodiment of the diagnostic testing system of this invention.
Figure 17:
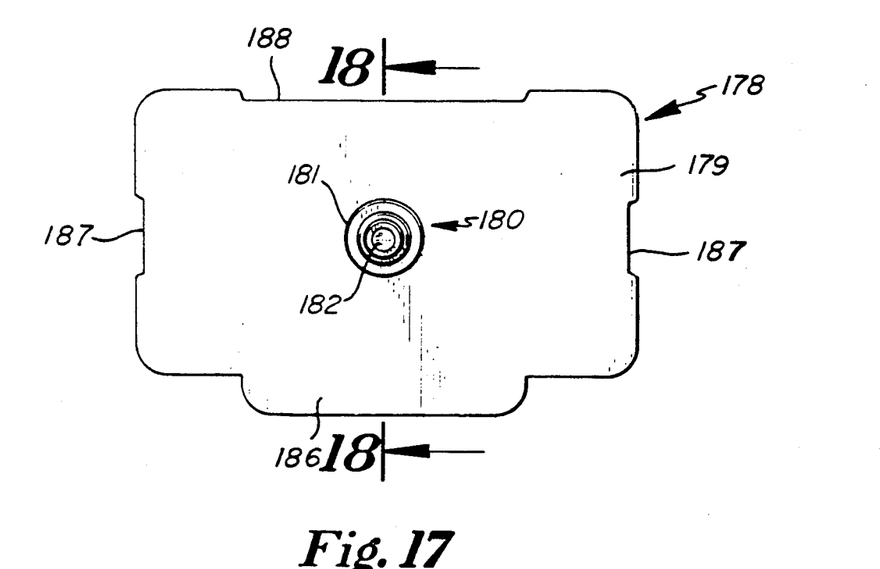
FIG. 17 is bottom view of the diagnostic testing system card structure of FIG. 16.
Figure 18:
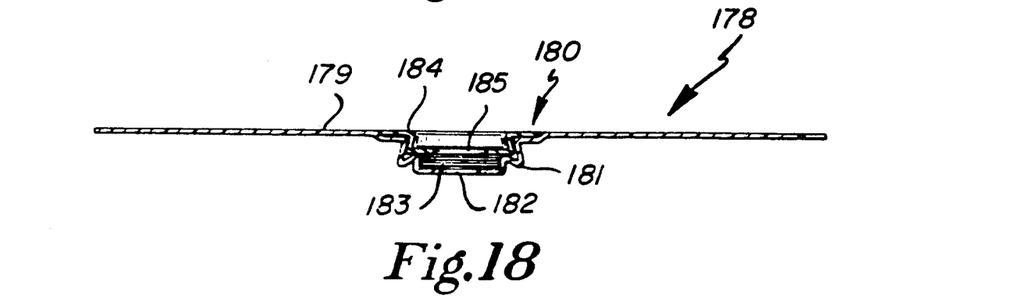
FIG. 18 is a sectional view of the diagnostic testing system card structure taken along line 18—18 of FIG. 16.

FIGS. 16–18 show another embodiment of the diagnostic device wherein the well structure 180 is shown positioned below the main planar body 179 of the card structure 178. Thus, in comparison to the card embodiment shown in FIGS. 1–5 and 8–12, the well structure 180 is positioned at a different height with respect to the horizontal plane of the card structure 178. It is within the purview of this invention that the well structure 180 can be positioned at any vertical position with respect to the horizontal plane of the card structure 178. Of primary importance, however, particularly when the card structure is used in the holder of a meter for analysis, is that the bottom well aperture is located at a fixed position so that the reading path of the meter is aligned with each bottom well aperture so as to provide consistent and reliable results.

Figure 23:
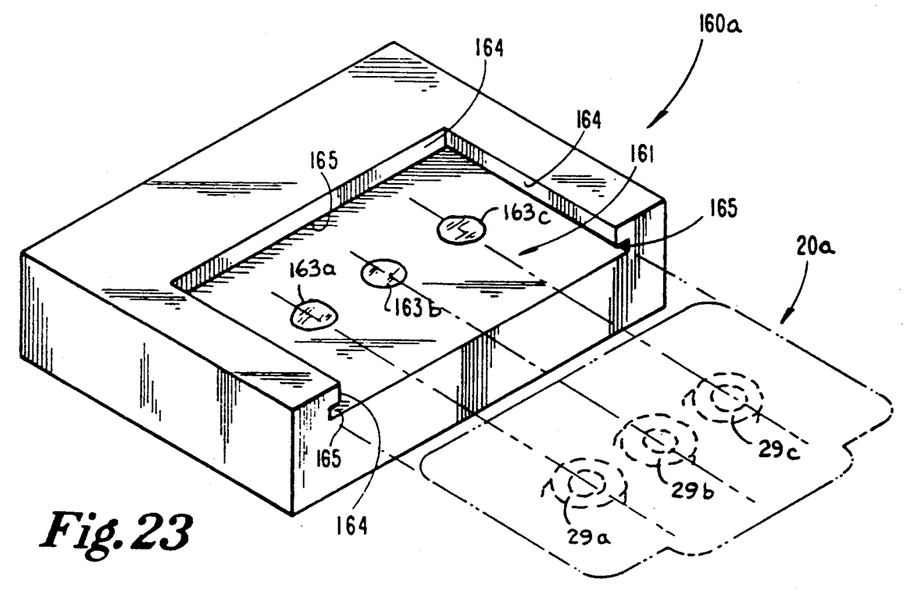
FIG. 23 is a perspective view of a reflectance-type meter suitable for receipt of a multiple reading test card.

Further shown in FIGS. 16 and 17 are a protruding card holding portion 186, as well as positioning slots 187 and 188. The holding portion 186 is designed to be grasped by the user of the card structure 178 so as to avoid contamination and possible contact with a blood sample, for example, as well as to identify the patient and to place test results. The positioning slots 187 and 188 are utilized for proper placement of the card structure 78 into the holder of a diagnostic meter so that the card and consequently the bottom aperture 182 is properly aligned and positioned with respect to the reading path of the meter. Alternatively or in addition, a recessed area in the meter reading surface to accommodate the well shown in FIG. 18 can be used for alignment purposes. The cupped wells shown in FIGS. 5, 12 and 18 can, therefore, be utilized to fit or mate into a corresponding female recess of a meter. The female recesses or indentations, although not shown in FIGS. 21 or 23, are located peripherally about the optical apertures 163 on the flat surface 62 and would fix the well in position for subsequent reading.

Figure 19:
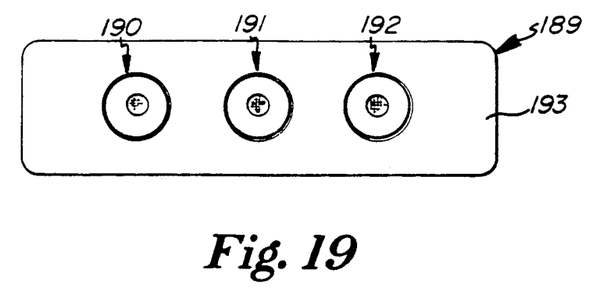
FIG. 19 is another embodiment of the diagnostic testing system and showing an elongated strip with multiple wells.

FIG. 19 shows a test strip 189 having a planar body 193 with a plurality of well structures 190–192. Although diagnostic card structures have been shown and discussed, it is possible to utilize the teachings of this invention, particularly those pertaining to the well structures 190–192, in rigid or semi-rigid structures such as in elongated test strips.

FIG. 20 shows an alternative embodiment of the system wherein the well enclosure 170 of body 194 has a plurality of layers or matrices 172–174 disposed therein between the retaining structure 171 with aperture 196 and the well bottom 176 with bottom aperture 177. Circumferential adjustment ridges 175, 197 and 198 are shown to extend inwardly from the well wall 195. This embodiment permits a variety of matrix compositions to be securely held within the well enclosure 170. The matrix 172–174 may consist of chemically impregnated papers, filters or membranes, or a combination thereof which are utilized to separate and/or react desired components of the blood or serum sample.

While specific embodiments for the test devices according to the present invention are disclosed, the general design, features and use are the same. The primary difference between the various embodiments is in the well structure configurations, design of the covers, how they snap into the central openings (pockets) of the test cards and the method in which the reagent pads are held in the annular receiving pocket which is part of the corresponding cylindrical portions.

A typical reagent chemistry pad 150 is illustrated in FIGS. 15 and 20 and includes a plurality of layers 150a, 150b, and 150c which are designed for the specific diagnostic test desired.

The diagnostic device structures shown and discussed are preferably of a rigid to semi-rigid composition. The rigidity allows more precise placement of the device into the optical block of the meter, thereby, increasing the accuracy and precision of the results. Suitable compositions include plastics, particularly those which can be molded or thermoformed. These materials also include biodegradable plastics, cardboard and board/plastic laminations. Such compositions provide economically feasible structures which are disposable and which can be discarded after use. Further, although generally planar and rectilinear card structures are shown and have been described, other shapes of the device can be utilized to provide the function of the diagnostic device structures of this invention.

In one of the preferred embodiments, the test card is shown to be similar in size to a business card (3.5 by 2.0 inches). The size of the card makes it easy to handle and the rounded corners prevent tearing of latex gloves. One card structure has been designed for use with a diagnostic meter. This card structure has specific dimensions and structure (compositions) suited for such use. However, alternative embodiments of the card structures are shown, for example, with multiple wells, or have structures for direct visualization and, thus, useable without a meter. Alternative embodiments do not necessarily require the specific dimensions set forth in these examples.

The devices of the present invention may be utilized in conjunction with a reflectance-type meter. Initially the device is removed from its packaging and inserted into the meter. The meter takes a color reading of the unreacted chemical pad which is visible on the bottom of the device through the apertures in the lower shelf of the cylindrical center portion. Then, a drop of blood or other fluid sample is introduced onto the center portion of the cover such that it is allowed to freely flow through the opening in the cover onto the first lamination of the reagent chemistry pad. The chemical reaction with the laminations of the pad by the blood occur layer by layer from the top through to the bottom of the pad. The meter then takes another color reading of the reacted (colored) chemical pad. The difference between these two readings is converted into a user-meaningful concentration value. Reading errors are minimized because the disposable diagnostic device is securely positioned in the meter and is not removed when the blood is applied. By securely fixing the position of the test device within the meter and not allowing that position to shift or vary, any variations which might be introduced into the reading are reduced or eliminated.

The configuration and size of the device also protects the meter from contamination by errant drops of samples, such as blood, serum, saliva or other body fluid. This reduces the need to clean and sterilize the reflectance-type meters and constitutes a significant advantage for end users such as hospitals and doctors' offices. The raised rib 24 (and 124) which extends about the perimeter of the respective test cards prevents blood drops from running off the edge of the card and, thus, reduces the risk of infection to the health care professionals involved in use of the present invention. The front flared tab on the card gives the card a definite visible orientation and provides the user with a positive grasping surface. Should the card, for example, be inserted backwards into the meter holder, the tab would prevent the card from seating properly therein.

In two embodiments of the card structure, the bottom surface of the card below the reagent pads is designed to be slightly lower than the rest of the card. This offset assures intimate contact of the disposable test card with the meter optics despite any minor dimensional changes to the card due to the thermoforming process, for example. Intimate contact of the disposable test card with the meter optics increases the accuracy of the reading. However, the bottom of the well structure may also be disposed above, directly level with, or below the plane of the card surface, as is also shown, depending upon either the type of meter device or visualization method used.

Positioning of the device in a meter can be achieved through card notches or indentations, as well as by the well or device protrusion. Thus, the well protrusion by itself can provide an excellent positioning feature of the device relative to the meter optics by utilizing a cooperating or mating surface in the meter.

The device size and configuration allows room for bar code graphics to be printed on the underneath side of the device, for example. This bar code, which is read by the meter during device insertion, may contain lot-specified data about the reagent chemistry. This data may further contain the critical parameters for the software algorithm within the meter electronics. Several glucose meters on the market today require the user to manually enter this data through entry buttons on the face of the meter.

Referring to FIGS. 21 and 22, meter 160 is illustrated without (FIG. 21) and with (FIG. 22) a test card inserted. In these examples, the receiving portion 161 of the meter includes a substantially flat surface 162 with a centrally disposed glass covered aperture 163 which is the window through which the meter takes readings of the color change which occurs in the chemistry reagent pad. The outer edge of surface 162 is bounded by a raised wall 164 which includes an undercut channel 165 for receipt of perimeter lip 21 (and 121) of the corresponding test cards. It is to be understood that the thickness of the perimeter lip is closely sized with the height of undercut channel 165 for a free, yet closely sized sliding fit of the card into the meter. The rectangular shape of the card and rectangular shape of the receiving portion of the meter and the presence of tab 22 (and 122) insures proper insertion and orientation of the card into the meter. Additionally outwardly extending and raised ribs 166 and 167 (shown in phantom line form) provide alignment and verification that the test card is fully seated. These ribs extend above and abut up against front edge 23 and define a clearance space 168 for tab 22. The opening in the cover which allows the drop of blood or other liquid to be introduced and reach the pad is coaxial with the lower apertures 40 and 138 and the lower aperture is accurately centered over the glass-covered aperture 163 of the meter to assure a full area for the meter to take its color and color change readings.

Referring to FIG. 23, there is illustrated another option for the present invention. In lieu of a single raised portion 29 on the test card and a single meter aperture 163, a plurality of each may be provided. In FIG. 23 meter 160a includes three aligned and evenly spaced apertures 163a, 163b and 163c. Test card 20a illustrated in phantom line form includes a corresponding aligned and spaced series of raised portions 29a, 29b and 29c. This multiple design allows three tests or readings to be made at the same time, for example, by the insertion of a single test card.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

That which is claimed is:

1. A diagnostic testing system for measuring an analyte in a sample, comprising:
   a) a semi-rigid structure of a predetermined size configuration;
   b) at least one cupped wall integral with and disposed in said structure and being positioned at a predetermined location, said cupped well having a wall of a predetermined depth, a to portion and bottom having means to permit transmission of a signal;
   c) a retaining means having an aperture, said retaining structure being for securement at the top portion of said cupped well and defining an interior volume for receiving and retaining a diagnostic element therein; and
   d) a raised rib structure integrally formed on the top surface of said structure and extending a predetermined distance thereabove.

2. The diagnostic testing system of claim 1, wherein said structure has a horizontal planar configuration, and wherein said cupped well wall intersects the horizontal plane of said structure.

3. The diagnostic testing system of claim 1, wherein said structure has a horizontal planar configuration, and wherein said cupped well wall is positioned above the horizontal plane of said structure.

4. The diagnostic testing system of claim 1, wherein said structure has a horizontal planar configuration, and wherein said cupped well wall is positioned below the horizontal plane of said structure.

5. The diagnostic testing system of claim 1, wherein said cupped well top portion has a circumferential groove, and wherein said retaining structure is a snap-fit cover and has a configuration to frictionally fit into said circumferential groove.

6. The diagnostic testing system of claim 1, wherein said structure has passive alignment means integrally formed therein, said means comprising at least one notch at a predetermined peripheral area of said structure.

7. The diagnostic testing system of claim 1, wherein said cupped well is constructed and arranged to provide alignment means for said structure for use in a meter.

8. The diagnostic testing system of claim 1, wherein said structure has a rectangular configuration and has the exterior dimensions of a semi-rigid card.

9. The diagnostic testing system of claim 1, wherein said retaining structure further has a grid structure spanning said aperture.

10. The diagnostic testing system of claim 1, wherein said structure is an elongated strip.

11. The diagnostic testing system of claim 1, wherein said structure has a plurality of cupped wells formed therein, each said well having a retaining structure.

12. The diagnostic testing system of claim 11, wherein one of said wells contains a control chemistry reagent.

13. The diagnostic testing system of claim 1, wherein said structure has informational data thereon.

14. The diagnostic testing system of claim 13, wherein said informational data includes data from the group consisting of a bar code, test meter calibration data, patient name, test provider name, and a chemistry lot identifier.

15. The diagnostic testing system of claim 1, wherein said signal is an optical signal, and wherein said means to permit transmission of a signal comprises an aperture in said cupped well bottom.

16. The diagnostic testing system of claim 15, wherein said well bottom has a transparent window covering said aperture.

17. The diagnostic testing system of claim 1, wherein said signal is an optical signal, and wherein said means to permit transmission of a signal comprises a substantially transparent region in said cupped well bottom.

18. The diagnostic testing system of claim 1, wherein said well wall has at least one circumferentially protruding ledge spatially positioned from said well bottom.

19. The diagnostic testing system of claim 18, wherein said well wall has a plurality of spatially parallel circumferential ledges, said retaining structure further having a peripheral edge for placement between adjacent ledges so as to provide an adjustable well depth to receive a range of matrix thicknesses.

20. The diagnostic testing system of claim 19, wherein a plurality of matrices are positioned in said cupped well in a layered configuration.

21. The diagnostic testing system of claim 1, further comprising a diagnostic element, said diagnostic element being for reacting the sample and generating an output signal corresponding to analyte concentration, said diagnostic element comprising at least one matrix which provides an output signal upon contact with an analyte of interest.

22. The diagnostic testing system of claim 21, wherein said matrix comprises at least one chemically impregnated layer.

23. The diagnostic testing system of claim 21, wherein said matrix provides an enzymatic reaction upon contact with the sample for the detection and quantitative measurement of an analyte therein.

24. The diagnostic testing system of claim 21, wherein said matrix provides an immunochemical reaction upon contact with the sample for the detection and quantitative measurement of an analyte therein.

25. The diagnostic testing system of claim 21, wherein said matrix is comprised of at least one filter layer and at least one chemically impregnated layer which is provided between said filter layer and said well bottom.

26. The diagnostic testing system of claim 21, wherein the system further comprises an optical meter having a software algorithm for providing a user-meaningful analyte concentration value via a signal from said reacted diagnostic element, and means for receiving said card structure therein.

27. The diagnostic testing system of claim 21, wherein the system further comprises a color chart having a plurality of color bars or codes corresponding to a range of analyte concentration values, said color chart being visually comparable with said reacted diagnostic element via said means for transmitting a signal.

28. A disposable diagnostic testing system for measuring an analyte in a sample, comprising:
   a) a semi-rigid elongated strip of a predetermined size and configuration and having a central axis;
   b) at least one cupped well integral with and vertically disposed in said strip and being positioned along said central axis, said cupped well having a predetermined well depth, an upper portion with a circumferential groove therein and a bottom portion with an aperture therethrough;
   c) a retaining structure having an aperture for placement in said circumferential groove of said cupped well; and d) at least one chemically impregnated matrix positioned in said cupped well between said retaining structure and said bottom for reacting a sample and generating an output signal measurable through said well bottom aperture.

29. The disposable diagnostic testing system of claim 28, wherein said elongated strip and retaining structure are constructed of a moldable material.

30. The disposable diagnostic testing system of claim 29, wherein said moldable material is a thermoplastic.

31. The disposable diagnostic testing system of claim 30, wherein said material is polystyrene.

32. A disposable diagnostic test system for detecting and measuring analyte concentration in a sample, comprising:
   a) a semi-rigid card structure of a predetermined size and having a substantially planar and rectangular configuration;
   b) at least one cupped well integral with and vertically disposed in said card structure, said cupped well having a top portion, a predetermined well depth, an upper circumferential groove in said well, at least one protruding ledge spatially positioned from said well bottom and being below said well top, and a bottom portion with an aperture therethrough;
   c) an annular snap-fit cover for placement in said circumferential groove of said cupped well; and
   d) at least one chemically impregnated diagnostic matrix layer for reacting a sample and generating an output signal representative of analyte concentration, said matrix being positioned in said cupped well between said annular cover and said well bottom.

33. The disposable diagnostic test system of claim 32, wherein said card and cover structures are constructed of a moldable material.

34. The disposable diagnostic test system of claim 33, wherein said moldable material is a thermoplastic material.

35. The disposable diagnostic test system of claim 34, wherein said material is polystyrene.

* * * * *